United States Patent [19]

Miki et al.

[11] Patent Number: 5,082,769
[45] Date of Patent: Jan. 21, 1992

[54] AQUEOUS SOLUTION OF TRIGLYCERIDE SUBSTRATE FOR DETERMINATION OF LIPASE

[75] Inventors: Iyoko Miki, Funabashi; Hiroyuki Tsubota, Chiba; Toshio Tsuchiko; Hisashi Ochi, both of Funabashi, all of Japan

[73] Assignee: Iatron Laboratories, Inc., Tokyo, Japan

[21] Appl. No.: 225,345

[22] Filed: Jul. 28, 1988

[30] Foreign Application Priority Data

Apr. 15, 1988 [JP] Japan ................................. 63-91688

[51] Int. Cl.$^5$ .................... C12Q 1/44; C12Q 1/34; G01N 33/92
[52] U.S. Cl. .......................................... 435/19; 435/18; 436/71; 436/164
[58] Field of Search ...................... 435/18, 19, 810; 436/71, 164; 34/5, 15; 260/398

[56] References Cited

U.S. PATENT DOCUMENTS

| | | | |
|---|---|---|---|
| 4,011,045 | 3/1977 | Bonderman | 436/13 |
| 4,179,334 | 12/1979 | Esders et al. | 435/21 |
| 4,282,001 | 8/1981 | Klose et al. | 23/230 |
| 4,309,502 | 1/1982 | Lauderdale | 435/810 |
| 4,343,897 | 8/1982 | Neumann et al. | 435/19 |
| 4,347,313 | 8/1982 | Proelss | 435/19 |

FOREIGN PATENT DOCUMENTS

| | | | |
|---|---|---|---|
| 0014252 | 8/1980 | European Pat. Off. | |
| 3342106 | 11/1982 | Fed. Rep. of Germany | |
| 2350604 | 2/1977 | France | |
| 58-156330 | 9/1983 | Japan | |
| 7403633 | 9/1975 | Netherlands | 436/71 |
| 8002697 | 12/1980 | PCT Int'l Appl. | 435/19 |

OTHER PUBLICATIONS

Bergmeyer, "Methods of Enzymatic Analysis", 1984, pp. 15–51.

Primary Examiner—Esther L. Kepplinger
Assistant Examiner—Toni R. Scheiner
Attorney, Agent, or Firm—Michael N. Meller

[57] ABSTRACT

A transparent and stable aqueous solution of a substrate for a determination of lipase, comprising triglyceride uniformly solubilized therein, a method for determination of lipase activity in a sample, employing the aqueous solution, and a process for the manufacture of a lyophilized product capable of forming the aqueous solution are disclosed. A process for the manufacture of a transparent and stable aqueous solution of triglyceride is also disclosed.

3 Claims, 2 Drawing Sheets

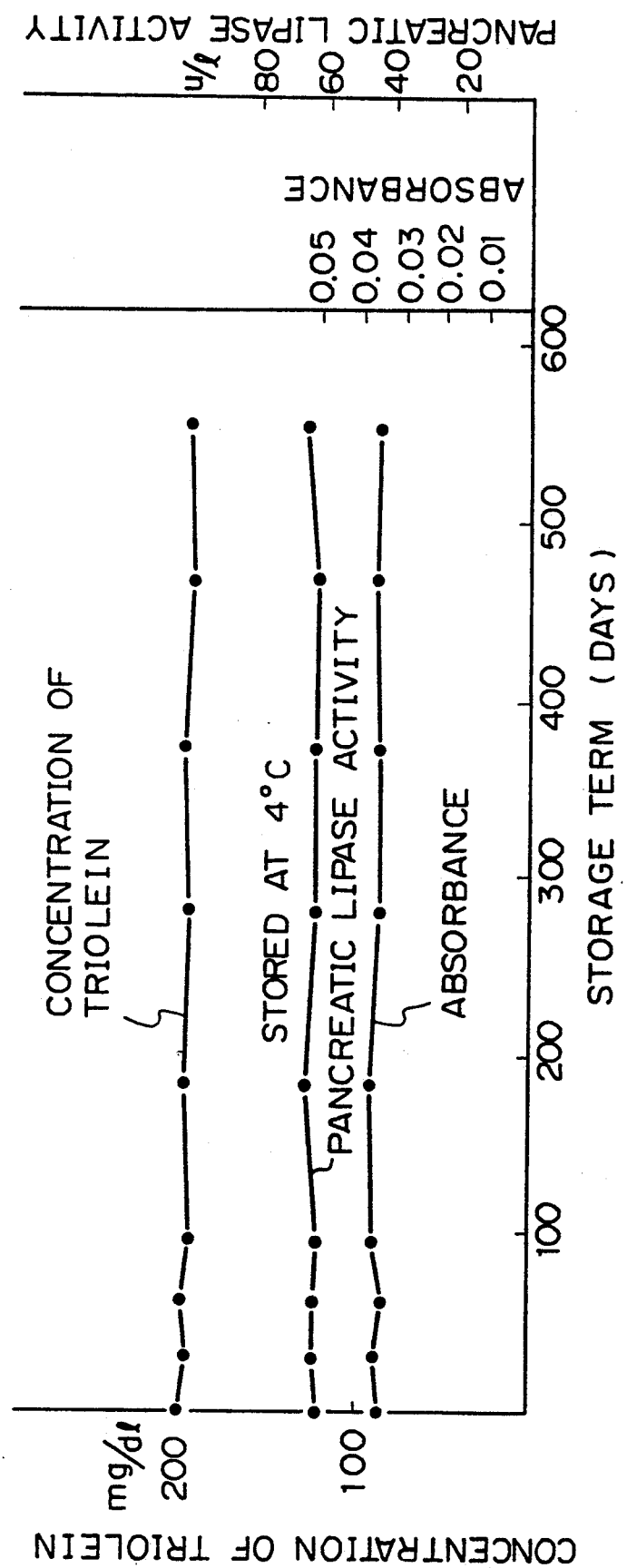

AQUEOUS SOLUTION OF TRIGLYCERIDE SUBSTRATE FOR DETERMINATION OF LIPASE

BACKGROUND OF THE INVENTION

1. Field of the Invention

The present invention relates to a transparent and stable aqueous solution of triglyceride substrate for a determination of lipase, a method for a determination of lipase activity in a sample, employing the aqueous solution, and a process for the manufacture of a lyophilized product capable of forming the aqueous solution. Further, the present invention also relates to a process for the manufacture of a transparent and stable aqueous solution of triglyceride.

2. Description of the Related Art

The enzyme lipase is naturally widely present in, for example, animals or plants, and the activity thereof is determined for various purposes; i.e., from a clinical point of view, it is particularly important for an early detection of diseases in pancreas, for example, acute pancreatitis, pancreas cancer, or the like.

Various methods for the determination of lipase are known, but the following two methods are most widely employed in the clinical field:

1. Nephelometry

This method comprises carrying out an enzymatic reaction while using a suspension of triglyceride (typically, olive oil) or glycerol ester of a higher fatty acid as a substrate, and then measuring a reduction of turbidity of the suspension by an absorbance thereof. But this method has the following disadvantages:

a) The lipase activity does not always coincide with the reduction of turbidity. For example, in emulsified samples, some samples show an increased absorbance.

b) The lipase activity is calculated from the measurement of the turbidity reduction. This is an indirect determination of the enzymatic activity c) When the lipase activity is low, the sensitivity and reproducibility are poor.

2. Method using synthesized substrate other than triglyceride

In this method, esters of fatty acid derivatives or alcohol derivatives, for example, monoglyceride, 1,2-diglyceride, p-nitrophenol laurate, dimethylcaprol tributyrate, α-naphthyl palmitate and the like are employed as a substrate. But, when the synthetic substrate is insoluble in water, this method encounters not only the disadvantages mentioned in the above item 1, but also a problem of a poor substrate-specificity such that the synthetic substrate may be hydrolyzed by esterases other than lipase. Although a water-soluble substrate can remedy the disadvantages mentioned in the above item 1, this method still has the problem of the substrate-specificity such that the substrate may be hydrolyzed by esterases other than lipase.

Under these circumstances, the inventors of the present invention carried out various research protects to develop a method for a determination of lipase, taking into account the following points:

a) Because lipase is the enzyme for hydrolyzing a triglyceride having long-chain fatty acids, triglyceride is used as the substrate.

b) Instead of measuring the reduction of the turbidity (substrate), the fatty acid, monoglyceride or glycerol formed from hydrolysis of triglyceride with lipase is directly measured c) The method is simple and can be applied for a clinical examination.

Japanese Examined Patent Publication (Kokoku) No. 59-39168 (Japanese Patent No. 1271605) discloses a process for the manufacture of a transparent solubilized aqueous solution of a water-insoluble material. This process comprises the steps of adding the water-insoluble material into an aqueous solution containing a nonionic surfactant, heating the whole, while stirring, to a temperature higher than a cloud point of the surfactant solution, and then cooling, while stirring, to a temperature of the cloud point or less to form a transparent solution. According to this Japanese Publication 59-39168, the aqueous solution thus obtained is very stable, and turbidity does not result from a change of the pH or a decrease of the concentration by dilution with water or buffer. This Japanese publication 59-39168 also teaches that the process is very useful for the manufacture of a stable standard solution of triolein, and that the transparent aqueous solution of triolein makes it possible to simply and accurately measure the lipase activity by a photometer. Although this Japanese Publication 59-39168 contains a relatively general description, it does not describe a concrete means of actually realizing a method for the determination of lipase activity in a sample.

In connection with the transparent solubilized aqueous solution of the water-insoluble material, the inventors of the present invention found another process for the manufacture thereof, as disclosed in Japanese Application No. 61-234520 filed on October 3, 1986 (published on April 21, 1988 as Unexamined Publication (Kokai) No. 63-91136).

Further, the inventors found that the transparent aqueous solution disclosed in Japanese Publication 59-39168 and Japanese Application 61-234520 can be employed as a substrate solution in the determination of lipase activity.

In addition, the inventors found that this transparent aqueous solution can be stored for a long term by a lyophilization thereof without any denaturation.

SUMMARY OF THE INVENTION

Accordingly, the object of the present invention is to provide a transparent aqueous solution of triglyceride substrate for a sensitive and effective determination of a very small amount of lipase, particularly in pancreatic juice, serum or the like.

Another object of the present invention is to provide a method for a determination of lipase, using the substrate solution.

Still another object of the present invention is to provide a process for the manufacture of a lyophilized product capable of forming the substrate solution.

Further, another object of the present invention is to provide a process for the manufacture of the transparent aqueous solution of triglyceride.

Other objects and advantages of the present invention will be apparent from the following description.

In accordance with the present invention, there is provided a novel transparent and stable aqueous solution of a substrate for a determination of lipase, comprising triglyceride uniformly solubilized therein.

Further, there is also provided a method for a determination of lipase activity in a sample, comprising the steps of placing the sample containing an unknown amount of lipase in contact with the aqueous solution, in the presence of the agent for accelerating a lipase activity, and optionally monoglyceride lipase, to form a fatty acid and glycerol, and carrying out a determination of the resulting fatty acid or glycerol, particularly by an absorption method, and then, for example, calculating the lipase activity in the sample from the result of the absorption method.

BRIEF EXPLANATION OF THE DRAWINGS

FIG. 2 is a graph showing a triolein concentration and absorbance (turbidity) of an aqueous substrate solution obtained from the lyophilized product according to the present invention, and lipase activity measured using the aqueous substrate solution.

DESCRIPTION OF THE PREFERRED EMBODIMENTS

Figure 1:
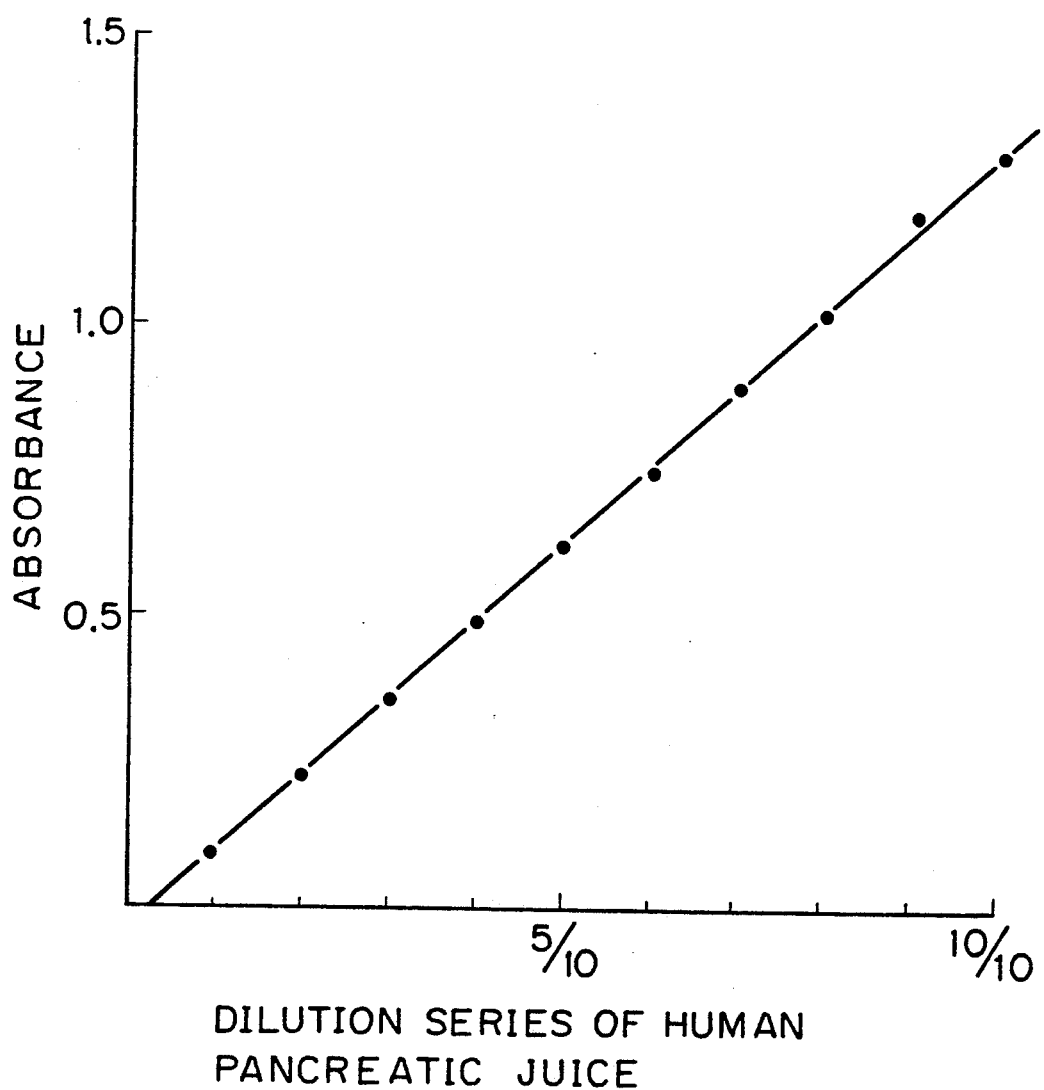
FIG. 1 shows the linearity of a relationship between a dilution series of human pancreatic juice and the absorbance measured in Example 3, and thus illustrates that the determination of lipase using the substrate of the present invention is quantitative.

The triglyceride which may be used in the present invention is an ester of fatty acids and a trivalent alcohol, i.e., glycerol, and is a product of an esterification of three hydroxyl groups in the glycerol with three fatty acids, having a general formula

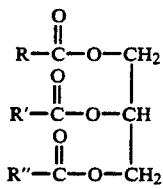

wherein RCOOH, R'COOH and R"COOH may be identical to or different from each other.

The following fatty acids may be used in the present invention:

1. Saturated fatty acids lauric acid $C_{11}H_{23}COOH$
myristic acid $C_{13}H_{27}COOH$
palmitic acid $C_{15}H_{31}COOH$
stearic acid $C_{17}H_{35}COOH$
arachic acid $C_{19}H_{39}COOH$
beheric acid $C_{21}H_{43}COOH$

2. Unsaturated fatty acids linderic acid $C_{12}H_{22}O_2$
lauroleic acid $C_{12}H_{22}O_2$
tsuzuic acid $C_{14}H_{26}O_2$
physeteric acid $C_{14}H_{26}O_2$
myristoleic acid $C_{14}H_{26}O_2$
palmitoleic acid $C_{16}H_{30}O_2$
petroselinic acid $C_{18}H_{34}O_2$
oleic acid $C_{18}H_{34}O_2$
elaidic acid $C_{18}H_{34}O_2$
vaccenic acid $C_{18}H_{34}O_2$
linoleic acid $C_{18}H_{32}O_2$
linolenic acid $C_{18}H_{30}O_2$
α-eleostearic acid $C_{18}H_{30}O_2$
β-eleostearic acid $C_{18}H_{30}O_2$
punicic acid $C_{18}H_{30}O_2$
parinaric acid $C_{18}H_{28}O_2$
gadoleic acid $C_{20}H_{38}O_2$
cetoleic acid $C_{22}H_{42}O_2$
erucic acid $C_{22}H_{42}O_2$
arachidonic acid $C_{20}H_{32}O_2$ The triglycerides of the general formula (I), wherein RCOOH, R'COOH and/or R"COOH are the fatty acids as mentioned above, are as follows: trilaurin (12, 12, 12: number of carbon atoms of bonded fatty acids), tridecanoin (13, 13, 13), trimyristin (14, 14, 14), tripentadecanoin (15, 15, 15), tripalmitin (16, 16, 16), trimargarin (17, 17, 17), tristearin (18, 18, 18), trinonadecanoin (19, 19, 19), triolein (18, 18, 18), trilaidene (18, 18, 18), trilinolein (18, 18, 18), trilinolenin (18, 18, 18), trierucin (22, 22, 22), tribrassidin (22, 22, 22), 1-lauro-dimyristin (12, 14, 14), 1-myristo-dipalmitin (14, 16, 16), 1-palmito-distearin (16, 18, 18), 1-stearo-dipalmitin (16, 16, 18), 2-stearo-dipalmitin (16, 18, 16), 2-palmito-distearin (18, 16, 18), 1-oleodistearin (18, 18, 18), 1-linoleo-distearin (18, 18, 18) 2-oleo-distearin (18, 18, 18), 1-stearo-diolein (18, 18, 18), 1-stearo-dilinolenin (18, 18, 18), 1-stearo-2-myristo-3-palmitin (18, 14, 16), 1-stearo-2-palmito-3-myristin (18, 16, 14), 1-lauro-2-myristo-3-palmitin (12, 14, 16).

When the human lipase is determined, preferably, as the substrate, the triglycerides having fatty acids present in the human body are used in a large amount. Examples of such fatty acids are myristic, palmitic, stearic, palmitoleic, oleic and linoleic acids, and the like. In particular, the preferable substrate comprises the triglycerides containing one or more (particularly, three) oleic acid which is the fatty acid believed to be naturally present widely and in the large amount, and present in the human body in the large amount.

The surfactant which may be used in the present invention is a nonionic surfactant, for example, a polyoxyethylene derivative such as polyoxyethylene lauryl ether, polyoxyethylene cetyl ether, polyoxyethylene stearyl ether, polyoxyethylene oleyl ether, polyoxyethylene octylphenyl ether, polyoxyethylene nonylphenyl ether, polyoxyethylene polyoxypropylene block copolymer, or polyoxyethylene higher alcohol. Hydrophilic-lipophilic balance (HLB) of the nonionic surfactant ranges preferably 8 to 20, more preferably 10 to 16. For the lipase reaction, polyoxyethylene higher alcohol (HLB: 10–16) is most preferable.

The substrate solution of the present invention may be prepared by using a process known per se, or processes found by the inventors of the present invention.

For example, the aqueous substrate solution may be prepared by mixing the triglyceride and the nonionic surfactant in an aqueous liquid (such as distilled water of buffer) at the temperature of the cloud point or higher of the liquid containing the surfactant, and then cooling, while stirring, to a temperature less than cloud point. In this process, the mixture of the triglyceride and the surfactant in the aqueous liquid is turbid even at the cloud point or higher. The triglyceride is mixed in the turbid liquid while stirring. Thereafter, while still continuing the stirring, the liquid is cooled to the temperature less than cloud point, and a transparent and stable substrate solution may be obtained. In many cases, the transparent solution thus obtained should be diluted with the aqueous liquid in order to yield the stable substrate solution.

When a crystalline solid triglyceride is used, it is preferable to dissolve the same in a minimum amount of alcohols prior to the mixing step. Further, the above mixing step includes various embodiments by combining a step of adding the water-insoluble material such as the triglyceride and the surfactant into the aqueous liquid, and a step of heating the aqueous liquid which may contain the water-insoluble material such as triglyceride and/or the surfactant. For example, the mixing step may comprise adding the water-insoluble material such as the triglyceride and the surfactant into the aqueous liquid, and then heating the resulting liquid. Further, the mixing step may comprise heating the aqueous liquid which contains none or either of the water-insoluble material such as the triglyceride or the surfactant, and then adding the surfactant and/or the water-insoluble material such as the triglyceride. Further, the cloud point of the aqueous liquid containing the nonionic surfactant can be raised or dropped by adding a cationic surfactant and/or an anionic surfactant. Therefore, the liquid containing the cationic and/or anionic surfactant in addition to the nonionic surfactant may be employed as the aqueous solution containing the nonionic surfactant in said mixing step.

The term "transparent" used herein with respect to the aqueous substrate solution means that the solution in question shows an absorbance of 0.2 or less, preferably 0.1 or less measured at 340 nm.

The term "stable" used herein with respect to the aqueous substrate solution means that the solution in question maintains the transparency as defined above for a period of time sufficient to use as a substrate solution for the measurement of the lipase activity, for example, 1 day or more, preferably 1 week or more.

Further, the inventors completed a novel process for the manufacture of the solubilized aqueous solution of the water-insoluble material. Accordingly, the present invention also relates to a process for the manufacture of a transparent and stable aqueous solution of a water-insoluble material including triglyceride, comprising the steps of adding the water-insoluble material such as the triglyceride while stirring in an aqueous liquid containing the nonionic surfactant, while the liquid is maintained at a temperature of a cloud point or higher of the surfactant liquid, although the cloud point has been dropped by an addition of a builder, and then diluting the resulting liquid with an aqueous liquid to thereby raise the cloud point to obtain the transparent solution.

Further, the present invention also relates to a transparent and stable aqueous solution of the water-insoluble material including triglyceride, comprising about 0.4 to 2 w/v % by weight of the water-insoluble material such as triglyceride, about 4 to 2 w/v % of nonionic surfactant, and about 0.4 to 2 w/v % of builder.

In the above process, the addition of the builder causes a depression of the cloud point, whereby the step of heating the turbid solution can become unnecessary. Further, the dilution of the turbid solution causes a reduction of the concentration of the builder, whereby the temperature of the solution falls below the cloud point without cooling, and then the transparent solution is formed.

The water-insoluble materials which may be solubilized are typically lipids, for example, monoglyceride, diglyceride, triglyceride, cholesterol, esterified cholesterol, phospholipid, or the like.

The nonionic surfactants as mentioned above may be used in this process.

The builders which may be used are, for example, sodium salts of inorganic or organic acids, such as sodium hydrogenphosphate, polyphosphate, carbonate, citrate or tungstate (alkaline salt); sodium sulfate or chloride (neutral salt); or sodium hydrogensulfate (acidic salt). In some cases, salts of other alkali metals or alkali earth metals can be used, if desired.

The selection of the builder used depends on the pH value of the solution of the water-insoluble material. For example, sodium tungstate is preferably used as the builder when the final solution of water-insoluble material is alkaline, because sodium tungstate causes turbidity under an acidic condition. Sodium tungstate does not cause a problem at a pH of 8.0, even if dissolved in an amount of 20% w/v.

In the above process, it is convenient to obtain the transparent aqueous solution of the water-insoluble material without carrying out the heating and cooling steps for elevating and dropping the temperature of the aqueous solution of the nonionic surfactant. Therefore, the concentration or the amount of the builder added is preferably determined so that the cloud point of the aqueous surfactant solution is made to fall below normal temperature. More particularly, when the transparent solution of the water-insoluble material is produced, the aqueous solution of the nonionic surfactant is first prepared, and then the selected builder is slowly added thereto. The amount of the builder added may be determined by observing the appearance of turbidity at room temperature. Note, the amount varies with the room temperature of each manufacturing atmosphere.

As the aqueous liquid containing the nonionic surfactant, the liquid which contains the cationic surfactant and/or the anionic surfactant in addition to the nonionic surfactant may be employed in the adding step.

As the liquid for diluting the turbid liquid, water or a buffer is usually employed. The dilution liquid is preferably selected by taking into account the pH value of the solution, as in the selection of the builder.

In the above process, it is necessary to continuously and vigorously mix the (turbid) aqueous liquid so that the water-insoluble material is solubilized to obtain the transparent solution. For this purpose, a stirring operation is generally carried out.

The above process for the manufacture of the transparent solution of the water-insoluble material wherein the builder is used may be employed for preparing the transparent aqueous solution of the triglyceride substrate.

In the transparent triglyceride substrate solution prepared with or without the builder, the lipase reaction, especially pancreatic lipase reaction, can be inhibited if an excess amount of the nonionic surfactant is present. In the adding step of the above-mentioned processes of the manufacture of the transparent solution, 1–40% by weight, (preferably 5 to 20% by weight) of the nonionic surfactant is preferably used and 0.05–0.5% by weight of the triglyceride such as triolein is preferably used, on the basis of 100% by weight of distilled water.

In the transparent triglyceride substrate solution of the present invention, the lipase reaction is performed preferably in the pH range of 4–11, more preferably 6–9. As the buffer, there may be used, for example, sodium citrate-phosphate buffer, imidazole hydrochloric acid buffer, triethanol amine hydrochloric acid-sodium hydroxide buffer, tris buffer, glycylglycine-sodium hydroxide buffer, diethanol amine-hydrochloric acid buffer, borate buffer, 2,4,6-trimethylpyridinehydrochloric acid buffer, phosphate buffer, and Good's buffer or the like. The buffer is preferably used in a concentration of about 5 mM to 300 mM.

Upon using the substrate solution of the present invention for the determination of the lipase (especially, pancreatic lipase) activity, it is essential to use an agent for accelerating the lipase activity, such as bile salt or colipase. For example, preferably about 1 mM–100 mM of bile salt, such as the salt of cholic acid, deoxycholic acid, lithocholic acid, glycocholic acid or taurocholic acid, and 50 U/test or more of colipase, is added to the substrate solution. The agent for accelerating the lipase activity may be incorporated in the substrate solution at any desired stage, for example, during the preparation of the solution, during the storage of the solution, or immediately before employing the solution, so long as the agent is present when the lipase reaction is performed.

Further, a greater effect is obtained if about 1 mM –80 mM of calcium chloride and about 5 mM–500 mM of sodium chloride are used in combination with the substrate solution.

The preferred transparent substrate solution according to the present invention comprises triglyceride and surfactant so that about 0.0005% by weight or more (preferably about 0.002 to 0.5% by weight) of triglyceride, and about 0.005% by weight or more (preferably about 0.02 to 4% by weight) of nonionic surfactant, are present in a final solution wherein the measurement of the lipase activity is perfomed. The amount of the builder added is that necessary for depression of the cloud point of the solution containing the surfactant used.

The aqueous triglyceride substrate solution thus obtained according to the present invention is a stable composition very useful for the determination of lipase activity in a sample.

As the sample to be analyzed in the present invention, there may be mentioned any liquid sample containing lipase, such as human pancreatic juice, human serum, plasma, urine, cell extract, and solution from culture medium.

In the method for the determination of the lipase activity according to the present invention, basic reactions comprise the lipase reaction of the solubilized triglyceride as the substrate to form fatty acids hydrolyzed with the lipase, and a reaction between the resulting fatty acid, adenosine triphosphate (ATP), and coenzyme A (CoA) in the presence of acyl-CoA synthetase (ACS). Thereafter, it is possible to measure either i) the adenosine monophosphate (AMP) formed, ii) the acyl CoA formed, or iii) the remaining CoA.

Examples of the above measuring methods i) to iii) will be explained hereinafter.

i) Methods for measuring AMP

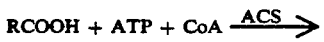

RCO — CoA + AMP + pyrophosphate ①

②

③

④

-continued or

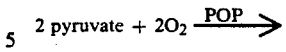

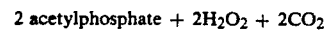

The formed AMP is reacted with ATP and phosphoenolpyruvate (PEP) in the presence of myokinase (MK) and pyruvate kinase (PK) to form pyruvate, and the resulting pyruvate is then reacted with nicotinamide adenine dinucleotide-reduced type (NADH) in the presence of lactate dehydrogenase (LDH). The reduction of the NADH is measured. Alternatively, the measurement is performed by colorimetry, using pyruvate oxidase (POP).

As examples of the measuring method i), there may be further mentioned a method for measuring ammonia using ADP deaminase, a method for measuring ammonia using AMP deaminase, a method for measuring ammonia using AMP nucleotidase or adenine deaminase, or a method for measuring ammonia using AMP pyrophosphorylase or adenine deaminase.

ii) Methods for measuring acyl-CoA

acyl-CoA + AMP + pyrophosphate ①

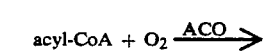

②

2-3.trans-enoyl-CoA + H$_2$O$_2$

In these methods, acyl-CoA is subjected to an action of acyl-CoA oxidase (ACO), and hydrogen peroxide is formed. The formed hydrogen peroxidase is measured by a peroxidase process, catalase process, or the like.

The hydrogen peroxide is measured by oxidation-condensation with 4-amino antipyrine and various couplers. The couplers are, for example, phenols, anilines, toluidines or the like, such as N-ethyl-N-sulfopropyl-m-toluidine, N,N-diethyl-m-toluidine, 3-methyl-N-ethyl-N-($\beta$-hydroxyethyl)-aniline, N-ethyl-N-(2-hydroxy-3-sulfopropyl)-m-toluidine, 3,5-dimethoxy-N-(3-sulfopropyl)-aniline. Alternatively, 3-methyl-2-benzothiazolinonehydrazone may be used instead of 4-aminoantipyrine. Further, couplers such as 10-(3-methoxycarboxyl-aminomethyl-benzoyl-carbamoyl)-3,7-bis(dimethyl-3 nk)-10H-phenothiazine, 3-bis(4-chlorophenyl) methyl-4-dimethyl-aminophenylamine may be used in the absence of 4-aminoantipyrine.

Alternatively, acyl-CoA may be directly applied to a $\beta$-oxidation system which is a main metabolic pathway of a fatty acid. More particularly, acyl-CoA is converted with acyl-CoA oxidase to 2–3 trans-enoyl-CoA. By the actions of anocyl-CoA hydratase, 3-hydroxyacyl-CoA dehydrogenase and 3-ketoacyl-CoA thiolase cause an increase of NADH, and this increase is measured.

iii) Methods for measuring remaining CoA

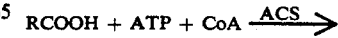

1

RCO — CoA + AMP + pyrophosphate

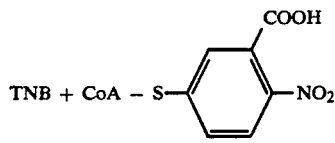

The remaining CoA may be measure a quantitative agent for SH groups, such as 5,5,'-dithiobis-2-nitrobenzoic acid (DTNB).

Instead of measuring fatty acids as in the above methods i) to iii), glycerol resulting from the lipase reaction may be measured. In the present method for determination, typically the lipase from the human body (e.g., pancreatic lipase, lipoprotein lipase, hepatic lipase) is employed. The human lipase hydrolyzes esters in 1- and/or 3-positions of the triglyceride, and thus it is necessary to incorporate monoglyceride lipase to obtain the glycerol being measured. The lipase from microorganisms can generally hydrolyzes esters in 1-, 2- and 3-positions of the triglyceride, and thus it is not necessary to employ monoglyceride lipase therewith.

In the present method for determination of the lipase activity, any absorption methods known to those skilled in the art may be used.

As briefly disclosed hereinbefore, the present invention also relates to a process for the manufacture of a lyophilized product.

Various methods have been developed and published wherein the solubilized aqueous solution is lyophilized, stored in the form of lyophilized powder, and then converted back into the original form by dissolving into water, upon use. Reference is made to, for example, Japanese Unexamined Patent Publication (Kokai) No. 60-224617 and No. 62-38. The conventional methods for lyophilization of the water-insoluble material comprise solubilizing or emulsifying the water-insoluble material in an aqueous solution with the nonionic surfactant, and optionally, adding an excipient or stabilizer and then carrying out a conventional lyophilization.

Conventional solubilized or emulsified aqueous solution which is converted back with water from the lyophilized product prepared from the original solubilized or emulsified aqueous solution by lyophilization, has the following disadvantages:

a) In the conventional methods, a powder cannot be obtained without employing a large amount of additives such as an excipient or stabilizer, upon lyophilization. In some cases, such additives become components insoluble in water when the lyophilized product is converted back to the aqueous solution. In particular applications of the aqueous solution converted from the lyophilized product, such additives serve as an inhibitor.

b) In general, if the aqueous solution is lyophilized before the water-insoluble material has been sufficiently solubilized therein, the conversion with water from the resulting lyophilized product cannot produce an aqueous solution which will sufficiently solubilize or emulsify the material. Therefore, various cumbersome techniques requiring a high degree of accuracy must be used to determine the kind and amount of the surfactant used, the solubilizing method, and the like. Hitherto, many cases have occurred wherein a sufficiently solubilized solution to be lyophilized cannot be obtained, in addition to many other problems that arose.

c) In the solubilized or emulsified solution converted back with water from the conventional lyophilized product, the water-insoluble material is merely emulsified and the converted solution is turbid and white or opaque, and thus cannot be used in some applications.

Under the above circumstances, the inventors of the present invention carried out various research projects to develop a process for the manufacture of a lyophilized product from which an excellent transparent aqueous solution of the water-insoluble material can be obtained, and thus discovered such a process. Further, the inventors found that such a lyophilization process may be applied to the transparent triglyceride substrate aqueous solution according to the present invention.

Accordingly, the present invention relates to a process for the manufacture of a lyophilized product capable of forming a transparent and stable aqueous solution of triglyceride substrate for a determination of lipase, comprising the steps of adding the triglyceride and the nonionic surfactant in an aqueous liquid at a temperature of a cloud point or higher of a liquid containing the surfactant; cooling, while stirring, to a temperature less than the cloud point to form a transparent solution; and then lyophilizing the thus obtained solution, optionally with an excipient or stabilizer.

Further, the present invention also relates to a process for the manufacture of a lyophilized product capable of forming a transparent and stable aqueous solution of triglyceride substrate for a determination of lipase, comprising the steps of adding the triglyceride while stirring in an aqueous solution containing a nonionic surfactant, while the solution is maintained at the temperature of the cloud point or higher of the nonionic surfactant solution, although the cloud point has been dropped by an addition of a builder; diluting the resulting liquid with an aqueous liquid to thereby reduce the concentration of the builder and raise the cloud point to obtain the transparent solution; and then lyophilizing the thus obtained solution, optionally with an excipient or stabilizer.

As the excipient which may be used in the present invention, there may be mentioned sucrose (1–10%), potassium chloride (5–10%), polyethyleneglycol (5–10%), polyvinyl pyrrolidone (5–10%), oligo sugars (1–10%), dextran (1–10%), albumin (1–5%), carboxymethylcellulose (1–10%), milk sugar (1–10%), glycine (5–10%), and Ficoll 400 (1–10%), or the like. Of those materials, sucrose, potassium chloride, oligo sugars, dextran, albumin, milk sugar (1–10%), glycine (5–10%) may be also used as a stabilizer. The numerical figures cited in parentheses above indicate the ranges of the amount of the materials used.

In the above lyophilization process of the present invention, any triglycerides, any nonionic surfactants and any builders (if employed) as mentioned above may be used.

The agent for accelerating the lipase (especially, pancreatic lipase) activity, such as colipase or bile salt, may be incorporated before the lyophilizing step. Alternatively, the agent may be added to the aqueous solution converted back with water from the lyophilized product.

In accordance with the present lyophilization process, the transparent aqueous solution of the triglyceride substrate according to the present invention can be lyophilized and stored in the form of the lyophilized powder, and then converted back with water or the buffer to the transparent solution which can be used for the determination of the lipase activity.

Although only triglyceride is explained as the material to be solubilized with respect to the present lyophilization process, other water-insoluble materials may be used. For example, cholesterols, phospholipids, glycolipids, fatty acids, neutral fats, glycerol ethers, waxes, cerebrosides, higher alcohols, fat-soluble vitamins (e.g., vitamin A, D, E, K, etc.), squalene, carotenoids, or aliphatic hydrocarbons (e.g., pentadecane, isooctadecane, etc.) also may be used instead of triglyceride.

EXAMPLES

The present invention now will be further illustrated by, but is by no means limited to, the following Examples.

EXAMPLE 1

A. Preparation of Reagents 1 to 4

(1) Reagent 1

After 10 g of Emulgen 707 (polyoxyethylene higher alcohol) as the nonionic surfactant was dissolved in 90 ml of distilled water, 5 g of sodium chloride (builder) was added, and the whole stirred at a room temperature (25° C.). The liquid then became turbid, and into the turbid liquid, 2 g of triolein was added and vigorously stirred for about 2 hours. The resulting liquid was diluted with 10 mM tris buffer (pH 7.9) to 100 times volume to obtain a transparent solution. Thereafter, sodium deoxycholate, (10 mM), sodium chloride (70 mM), calcium chloride (5 mM), and colipase (30,000 U/dl) were added to the transparent solution to yield the reagent 1.

(2) Reagent 2

The reagent 2 was prepared by dissolving acyl-CoA synthetase (5.0 U/5 ml), adenosine 5′-triphosphate (33.0 μmol/5 ml) and lithium salt of CoA (7.0 μmol/20 ml) in an aqueous solution containing trishydroxymethylaminomethane (0.05M, pH 7.85) and magnesium chloride hexahydrate (5 mM).

(3) Reagent 3

The reagent 3 was prepared by dissolving acyl-CoA oxidase (10.0 U/20 ml), peroxidase (20,000 U/20 ml) and 4-aminoantipyrine (24 μmol/20 ml) in an aqueous solution (pH 7.30) containing N,N-bis-(2-hydroxyethyl)-2-aminoethane sulfate (20 mM) and N-ethyl-N-sulfopropyl-m-toluidine (0.75 mM).

(4) Reagent 4

The reagent 4 was prepared by dissolving N-ethylmaleimide (10 mM) in an aqueous hydrochloric acid solution and adjusting a pH value to 3.0.

B. Measurement and Results

Each of 20 μl of purified water (control) and 20 μl of pancreatic juice (analyte) was added to a test tube containing 1.1 ml of the reagent 1, and incubated at 37° C. for 10 minutes. Then, 1 ml of the reagent 2 was added. After a reaction was carried out for 10 minutes, 1 ml of the reagent 4 was added. After 2 minutes, the reagent 3 was added and allowed to stand at a room temperature for another 10 minutes, and the absorbance was then measured at 550 nm to obtain 0.420 for the pancreatic juice with respect to the control of the purified water.

An aqueous solution of oleic acid (1,000 μeq/l) was prepared and used as a lipase standard solution (100 U/l). The same procedure as the above analyte was repeated, except that 20 μl of the standard solution was used. The absorbance was 0.104, and thus the lipase activity of the pancreatic juice was 403.8 U/l.

EXAMPLE 2

A. Preparation of Reagents 1 to 4

(1) Reagent 1

After 10 g of Emulgen 709 (polyoxyethylene higher alcohol; cloud point 56° C.) as the nonionic surfactant was dissolved in 90 ml of distilled water, the solution was heated to 56° C. or more. The solution reached the cloud point thereof and became turbid, and to the turbid liquid, 2 g of trilinolein was added and the whole was stirred for about 30 minutes, while maintaining the temperature thereof at 56° C. or more. The heating was then stopped, and the liquid was allowed to stand while stirring. As the temperature of the liquid dropped to room temperature, the liquid became transparent, and after the liquid became transparent, it was diluted with a distilled water to 10 times volume to obtain the solubilized substrate solution for lipase. This solution was designated as the reagent 1.

(2) Reagent 2

The reagent 2 was prepared by dissolving sodium deoxycholate (4.16 mg), sodium chloride (4.16 mg), calcium chloride (0.06 mg), and colipase (230 U) in 1.0 ml of an aqueous solution of trishydroxymethylaminomethane (10 mM, pH 7.9).

(3) Reagent 3

The reagent 3 was prepared by dissolving ATP (0.79 mg), phosphoenolpyruvic acid (0.15 mg), myokinase (7 U), pyruvate kinase (30 U), and lactate dehydrogenase (8 U) in 0.5 ml of an aqueous solution of trishydroxyethylaminomethane (10 mM, pH 7.9).

(4) Reagent 4

The reagent 4 was prepared by dissolving lithium salt of CoA (1.8 mg), acyl-CoA synthetase (4 U), and magnesium chloride (0.6 mg) in 1.0 ml of an aqueous solution of trishydroxyethylaminomethane (10 mM, pH 7.9).

B. Measurement and Results

Into a reaction cell, 100 μl of the reagent 1, 0.5 ml of the reagent 3, 1 ml of the reagent 4, and 20 μl of human pancreatic juice (analyte) were sequentially charged, stirred, and pre-incubated. The reagent 2 (1.0 ml) was added as a reaction initiator and the reaction was performed at 37° C. As a reagent blank, the reaction was also carried out without the analyte.

The lipase in the pancreatic juice was reacted with the solubilized substrate to yield fatty acid, and the resulting fatty acid was reacted with CoA and ATP in the presence of acyl-CoA synthetase. The formed AMP was converted in the presence of ATP and myokinase to ADP, which was reacted with phosphoenolpyruvate in the presence of pyruvate kinase to yield pyruvate. The formed pyruvate was subjected to the action of lactate dehydrogenase, and the reduction of NADH was measured by the absorbance at 340 nm. The absorbance fell in proportion to the reaction time. The reduction of the absorbance per 5 minute was 0.061, from which the lipase activity was calculated as 128.5 U/l.

EXAMPLE 3

A. Preparation of Reagents 1 to 3

(1) Reagent 1

After 10 g of Emulgen 709 (polyoxyethylene higher alcohol; cloud point 56° C.) as the nonionic surfactant was dissolved in 90 ml of distilled water, the solution was heated to 56° C. or more. The solution reached the cloud point thereof and became turbid, and to the turbid liquid, 2 g of triolein was added and the whole was stirred for about 30 minutes, while maintaining the temperature thereof at 56° C. or more. The heating was then stopped, and the liquid was allowed to stand while stirring. As the temperature of the liquid dropped to room temperature, the liquid became transparent. After the liquid became transparent, it was diluted with tris buffer (10 mM, pH 7.9) to 200 times volume. Thereafter, sodium deoxycholate, (2.5 mM), sodium chloride (35 mM), calcium chloride (3.5 mM), and colipase (30,000 U/dl) were added to the transparent solution to yield the reagent 1.

Reagent 2

The reagent 2 was prepared by dissolving acyl-CoA synthetase (66 U/dl), acyl-CoA oxidase (90 U/dl), peroxidase (16,000 U/dl), ATP (140 μmol), CoA (16 μmol), and 10-(3-methoxycarboxylaminomethylbenzoyl-carbamoyl)-3,7-bis(dimethylamino)-10H-phenothiazine (2.2 μmol) in Good's buffer (25 mM, pH 6.75).

(3) Reagent 3

As a control reagent, the reagent 3 was prepared by omitting triolein, colipase, and calcium chloride form the reagent 1.

B. Measurement and Results

Into two test tubes, 1 ml of the reagent 1 or the reagent 3, and then 20 μm of human serum were added, respectively. After the reaction was performed at 37° C. for 5 minutes, 1.5 ml of the reagent 2 was added into each tube. The temperature was maintained at 37° C. for 5 minutes and the absorbances were then measured at 666 nm.

As a standard, an aqueous oleic acid solution (1000 μeq/1) was prepared and used as a lipase standard solution (200 U/1).

In the following Table I, the absorbance value (calculated by subtracting that of the control from that of the analyte), and the lipase activity (calculated by using the standard solution) are listed for 10 samples of human sera and a standard solution.

TABLE I

|  |  | Absorbance | Lipase activity U/l |
|---|---|---|---|
| Standard solution | 200 U/1 | 0.4716 | 200 |
| Human serum | 1 | 0.0867 | 36.8 |
| Human serum | 2 | 0.0631 | 26.8 |
| Human serum | 3 | 0.0473 | 20.1 |
| Human serum | 4 | 0.0677 | 28.7 |
| Human serum | 5 | 0.0861 | 36.5 |
| Human serum | 6 | 0.1576 | 66.8 |
| Human serum | 7 | 0.1360 | 57.7 |
| Human serum | 8 | 0.2549 | 108.1 |
| Human serum | 9 | 0.3195 | 135.5 |
| Human serum | 10 | 0.0666 | 28.2 |

Further, a series of diluted solutions of human pancreatic juice was prepared, and the lipase activities thereof were measured in accordance with Example 3B. The results are shown in FIG. 1, which shows a very high linearity.

EXAMPLE 4

A. Preparation of Reagents 1 to 4

(1) Reagent 1

The following ingredients were dissolved in 25 ml of an aqueous solution of trishydroxymethylaminomethane (1.0M, pH 7.5) containing magnesium chloride (0.6 g/l) and calcium chloride (0.6 g/l) to yield the reagent 1.

| Adenosine 5'-triphosphate | 97 mg |
|---|---|
| Phosphoenolpyruvic acid | 14.6 mg |
| Lactate dehydrogenase | 840 U |
| Myokinase | 700 U |
| Pyruvate kinase | 940 U |
| Nicotinamide adenosine dinucleotide-reduced type | 24.5 mg |
| Lithium salt of CoA | 90 mg |
| Acyl-CoA synthetase | 196 U |
| Solubilized substrate (Reagent 1 in Example 2) | 1.4 ml |
| Colipase | 35,000 U |

(2) Reagent 2

The reagent 2 was prepared by dissolving 2 g of sodium deoxycholate in 100 ml of an aqueous solution of trishydroxyethylaminomethane (0.1M, pH 8.3).

(3) Reagent 3

As a conventional substrate suspension of triolein, the reagent 3 was prepared by adding the following ingredients into tris buffer (0.1M, pH 9.2).

| Triolein | 0.3 mM |
|---|---|
| Sodium deoxycholate | 17 mM |
| Sodium chloride | 35 mM |
| Calcium chloride | 1 mM |
| Colipase | 210,000 U/l |

B. Measurement and Results

Into an autoanalyzer (Hitachi 705 Autoanalyzer), 350 μl of the reagent 1 according to the present invention and 10 μl of human serum as an analyte were charged. After a reaction to eliminate free fatty acids in the human serum was carried out for 5 minutes, 50 μl of the reagent 2 was charged. The reduction from the absorbance measured 3 minutes later to that measured 5 minutes later was determined.

Into the same autoanalyzer, 500 μl of the reagent 3 as the conventional suspension and 20μl of human serum were charged, and the reduction from the absorbance measured 4 minutes later to that measured 5 minutes later was determined. The results are shown in Table II.

TABLE II

| | Analyte 1 | | | Analyte 2 | |
|---|---|---|---|---|---|
| | Method using substrate of the present invention | Conventional method | | Method using substrate of the present invention | Conventional method |
| 1 | 3.1 | −4 | 1 | 30.5 | 249 |
| 2 | 3.1 | 2 | 2 | 30.0 | 236 |
| 3 | 3.0 | 20 | 3 | 30.4 | 230 |
| 4 | 3.1 | 24 | 4 | 30.4 | 239 |

TABLE II-continued

| | Analyte 1 | | | Analyte 2 | |
|---|---|---|---|---|---|
| | Method using substrate of the present invention | Conventional method | | Method using substrate of the present invention | Conventional method |
| 5 | 3.2 | 25 | 5 | 30.3 | 240 |
| 6 | 3.3 | 1 | 6 | 30.4 | 246 |
| 7 | 3.0 | 29 | 7 | 31.0 | 246 |
| 8 | 3.0 | 11 | 8 | 30.9 | 258 |
| 9 | 3.0 | 13 | 9 | 30.8 | 264 |
| 10 | 3.0 | 11 | 10 | 31.1 | 262 |
| n | 10 | 10 | n | 10 | 10 |
| $\bar{x}$ | 3.08 U/l | 13.2 U/l | $\bar{x}$ | 30.58 U/l | 247.0 U/l |
| SD | 0.103 | 11.21 | SD | 0.352 | 11.37 |
| CV | 3.55% | 84.95% | CV | 1.15% | 4.60% |

In Table II, n denotes the number of runs performed, $\bar{x}$ denotes an average value, SD denotes a standard deviation, and CV denotes a coefficient of variation.

It is apparent from Table II that the method using the solubilized substrate solution of the present invention exhibits an excellent concurrent-reproducibility of the measurement results.

EXAMPLE 5

A. Preparation of Reagents 1 and 2

(1) Reagent 1

The following ingredients were dissolved in 15 ml of an aqueous solution of trishydroxymethylaminomethane (0.1M, pH 8.3) to yield the reagent 1.

| | |
|---|---|
| Solubilized triolein substrate (Reagent 1 of Example 2) | 1.7 ml |
| Calcium chloride | 100 mg |
| Magnesium chloride | 8 mg |
| Colipase | 14,000 U |
| (2) Reagent 2 | |
| Reagent 2 (a) | |
| Glycerokinase | 5.38 U |
| Peroxidase | $13.5 \times 10^4$ U |
| Adenosine triphosphate | 42.4 mg |
| L-α-glycerophosphate oxidase | 161 U |
| 4-aminoantipyrine | 5.7 mg |
| Ascorbate oxidase | 53.8 U |
| Reagent 2 (b) | |
| N,N-bis(2-hydroxyethyl)-2-aminoethane sulfonic acid | 4.27 g |
| N-ethyl-N-sulfopropyl-m-toluidine | 0.14 g |
| Magnesium chloride hexahydrate | 3.05 g |
| Triton X-100 | 0.1 g |
| Water | q.s. to 1,000 ml |
| pH adjusted to 6.65 | |

The reagent 2 was prepared by dissolving the reagent 2(a) in 36 ml of the reagent 2(b).

B. Measurement and Results

The reagent 1 (1.5 ml) and the reagent 2 (1.5 ml) were admixed with 20 μl of lipase (30 U/ml) obtained from yeast, and stirred at 37° C. for 5 minutes. As a reagent blank, the same procedure was repeated without lipase. The absorbance at 550 nm (subtracting the absorbance of the control) was 0.140, from which the lipase activity was calculated as 257 U/l, using the glycerol standard solution.

EXAMPLE 6

A. Preparation of Reagent (1) Reagent 1

The reagent 1 was prepared from the following ingredients:

| | |
|---|---|
| Solubilized substrate (Reagent 1 of Example 2) | 50 μl/ml |
| Colipase | 1200 U/ml |
| Calcium chloride | 3.5 mM |
| Sodium deoxycholate | 6.0 mM |
| Monoglyceride lipase | 3.0 U/ml |
| Glycerol dehydrogenase | 15 U/ml |
| Nicotinamide adenosine dinucleotide-oxidized type | 6.0 mM |
| Dihydroxyacetone kinase | 2.0 U/ml |
| Adenosine 5'-triphosphate | 4.0 mM |
| Magnesium chloride | 2.0 mM |
| Trishydroxymethylamino-methane-hydrochloric acid buffer (pH 8.5) | 100 mM |

B. Measurement and Result

The reagent 1 (500 μl) was admixed with human serum (20 μl). After 2 minutes, the increase of the absorbance at 340 nm was measured for 3 minutes, and was found to be 0.036 per 3 minutes. The lipase activity was calculated therefrom as 50.2 U/l.

It is believed that the reactions in this Example occurred as follows:

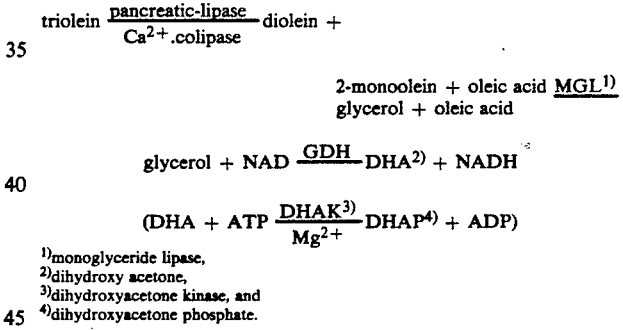

[1] monoglyceride lipase,
[2] dihydroxy acetone,
[3] dihydroxyacetone kinase, and
[4] dihydroxyacetone phosphate.

EXAMPLE 7

After 7 g of Emulgen 709 (polyoxyethylene higher alcohol; cloud point 56° C.) as the nonionic surfactant was dissolved in 63 ml of distilled water, the solution was heated to 56° C. or more. The solution reached the cloud point thereof and became turbid, and to the turbid liquid, 1.4 g of triolein was added and the whole was stirred for about 30 minutes, while maintaining the temperature at 56° C. or more. The heating was then stopped, and the liquid was allowed to stand while stirring. As the temperature of the liquid dropped to room temperature, the liquid became transparent, and after the liquid became transparent, it was diluted with 630 ml of an aqueous solution containing 3% of Ficoll 400 (water-easily-soluble synthetic polymeric compound prepared from sucrose and epichlorohydrin; molecular weight about 400,000; Pharmacia) as the excipient and 2% of sucrose as the stabilizer.

The resulting aqueous solution was charged in vials (25 ml vessel for lyophilization) at an amount of 5 ml/vial.

The solutions were frozen by cooling to −50° C., and dried under vacuum to obtain 140 vials containing 0.352–0.367 g/vial (moisture content 2% or less) of lyophilized powder containing triolein as the water-insoluble material.

EXAMPLE 8

After 10 g of Emulgen 707 (polyoxyethylene higher alcohol) as the nonionic surfactant was dissolved in 90 ml of distilled water, 5 g of sodium chloride (builder) was added, and stirred at a room temperature (25° C.). The liquid became turbid, and into the turbid liquid, 2 g of triolein was added and vigorously stirred for about 2 hours. The resulting liquid was diluted with 10 mM tris buffer (pH 7.9) to 10 times volume to obtain a transparent solution. Thereafter, sodium deoxycholate (10 mM), sodium chloride (70 mM), and colipase (30,000 U/dl) were added to the transparent solution. Into the resulting transparent solution, Ficol 400 (3%) as the excipient and sucrose (2%) as the stabilizer were added.

The resulting aqueous solution was charged in vials at an amount of 5 ml/vial, frozen by cooling to −50° C., and dried under vacuum to obtain 200 vials containing 0.543–0.560 g/vial (moisture content 2% or less) of lyophilized powder containing triolein as the water-insoluble material.

EXAMPLE 9

After 10 g of Emulgen 709 (polyoxyethylene higher alcohol: cloud point 56° C.) as the nonionic surfactant was dissolved in 90 ml of distilled water, 10 g of sodium chloride (builder) was added, and stirred at a room temperature (25° C.). The liquid became turbid, and into the turbid liquid, 1 g of lecithin was added and vigorously stirred for about 3 hours. The resulting liquid (still turbid) was diluted with 900 ml of an aqueous solution containing 5% of lactate.

The resulting aqueous solution was charged in vials at an amount of 5 ml/vial, frozen by cooling to −50° C., and dried under vacuum to obtain 200 vials containing 0.405–0.422 g/vial (moisture content 2% or loss) of lyophilized powder containing lecithin as the water-insoluble material.

EXAMPLE 10

After 10 g of Emulgen 810 (polyoxyethylene higher alcohol; cloud point 60° C.) as the nonionic surfactant was dissolved in 90 ml of distilled water, the solution was heated to 60° C. or more. The solution reached the cloud point thereof and became turbid, and to the turbid liquid, 2 g of vitamin E was added and the whole was stirred for about 30 minutes, while maintaining the temperature at 60° C. or more. The heating was then stopped, and the liquid was allowed to stand while stirring. As the temperature of the liquid dropped to room temperature, the liquid became transparent, and after the liquid became transparent, it was diluted with 900 ml of an aqueous solution containing 5% of polyethyleneglycol 6000 as the excipient.

The resulting aqueous solution was charged in vials at an amount of 5 ml/vial, frozen by cooling to −50° C., and dried under vacuum to obtain 200 vials containing 0.385–0.400 g/vial (moisture content 2% or less) of lyophilized powder containing vitamin E as the water-insoluble material.

EXAMPLE 11

After 10 g of Emulgen 709 (polyoxyethylene higher alcohol; cloud point 56° C.) as the nonionic surfactant was dissolved in 90 ml of distilled water, the solution was heated to 56° C. or more. The solution reached the cloud point thereof and became turbid, and to the turbid liquid, 2 g of trilinolein was added and the whole was stirred for about 30 minutes, while maintaining the temperature of 56° C. or more. The heating was then stopped, and the liquid was allowed to stand while stirring. As the temperature of the liquid dropped to room temperature, the liquid became transparent, and after the liquid became transparent, it was diluted with 1900 ml of TAPS buffer (10 mM, pH 8.6) containing 1.5% of Ficoll 400 (excipient) and 1% of sucrose (stabilizer).

The resulting aqueous solution was charged in vials at an amount of 5 ml/vial, freezed by cooling to −50° C., and dried under vacuum to obtain 400 vials containing 0.298–0.316 g/vial (moisture content 2% or less) of lyophilized powder containing trilinolein as the water-insoluble material.

EXAMPLE 12

1) The lyophilized powder in the vial obtained in Example 6 was dissolved by adding 5 ml of distilled water thereto, and the absorbance (turbidity) at 340 nm was measured to examine concurrent-reproducibility. The results for 50 vials are shown in Table III. It is apparent from Table III that the aqueous liquid converted back from the lyophilized powder has high transparency and only small variation among the vials.

TABLE III

| Sample No. | Absorbance |
|---|---|
| 1 | 0.036 |
| 2 | 0.036 |
| 3 | 0.038 |
| 4 | 0.037 |
| 5 | 0.034 |
| 6 | 0.035 |
| 7 | 0.036 |
| 8 | 0.036 |
| 9 | 0.037 |
| 10 | 0.037 |
| 11 | 0.034 |
| 12 | 0.036 |
| 13 | 0.035 |
| 14 | 0.036 |
| 15 | 0.037 |
| 16 | 0.036 |
| 17 | 0.038 |
| 18 | 0.036 |
| 19 | 0.035 |
| 20 | 0.038 |
| 21 | 0.036 |
| 22 | 0.037 |
| 23 | 0.036 |
| 24 | 0.036 |
| 25 | 0.037 |
| 26 | 0.035 |
| 27 | 0.034 |
| 28 | 0.036 |
| 29 | 0.038 |
| 30 | 0.037 |
| 31 | 0.037 |
| 32 | 0.036 |
| 33 | 0.036 |
| 34 | 0.038 |
| 35 | 0.036 |
| 36 | 0.037 |
| 37 | 0.036 |

TABLE III-continued

| Sample No. | Absorbance |
|---|---|
| 38 | 0.037 |
| 39 | 0.036 |
| 40 | 0.036 |
| 41 | 0.037 |
| 42 | 0.036 |
| 43 | 0.038 |
| 44 | 0.036 |
| 45 | 0.037 |
| 46 | 0.036 |
| 47 | 0.037 |
| 48 | 0.035 |
| 49 | 0.038 |
| 50 | 0.036 |

N = 50
Mean = 0.03632
S.D = 0.001038
C.V = 2.860
Max = 0.038
Min = 0.034
Range = 0.004

2) Fifty vials obtained in Example 6 were stored at 4° C. for 0 to 550 days. The lyophilized powder was sequentially converted back with 5 ml of distilled water to an aqueous solution. For the converted solution, the content of triolein was measured by a conventional method for a determination of triglyceride after eliminating free glycerol, and the absorbance (turbidity) at 340 nm was also measured, and the lipase activity was measured in accordance with the procedure in Example 4. The results are shown in FIG. 2.

It is clear from FIG. 2 that the lyophilized product prepared according to the present invention can stably form the aqueous solution containing solubilized triolein at a constant content while exhibiting a constant turbidity and maintaining the lipase activity, for a long storage term.

EXAMPLE 13

After 10 g of Emulgen 709 (polyoxyethylene higher alcohol; cloud point 56° C.; Kao Atlas K. K.) as the nonionic surfactant was dissolved in 90 ml of distilled water, 10 g of sodium sulfate (builder) was added, and stirred at a room temperature (25° C.). The liquid became turbid, and into the turbid liquid, 1 g of triolein was added and vigorously stirred for about 3 hours. The resulting turbid liquid was diluted with 50 mM BES buffer (pH 6.8) to 10 times volume to obtain a transparent solution.

The content of triolein in the resulting aqueous triolein solution was measured in a conventional manner using a measuring agent for neutral fatty acid. The calculated content of triolein was 99.6 mg/dl (based on theoretical value of 100 mg/dl).

The absorbance of the resulting aqueous solution was also measured at 340 nm, on the basis of distilled water, to obtain 0.024.

The resulting aqueous solution was stored for 3 months at 4° C., 25° C. or 37° C. The triolein content measured 3 months later had not changed from said value for each solution. Further, each solution after 3 months was very stable without turbidity.

EXAMPLE 14

After 4 g of Emulgen 507 (polyoxyethylene higher alcohol; cloud point 50° C.; Kao Atlas K. K.) as the nonionic surfactant was dissolved in 90 ml of distilled water, 10 g of sodium chloride (builder) was added, and stirred at room temperature (25° C.). The liquid became turbid, and into the turbid liquid, 0.4 g of triolein was added, and vigorously stirred for about 3 hours. The resulting turbid liquid was diluted with distilled water to 4 times volume to obtain a transparent solution.

The content of triolein in the resulting aqueous triolein solution was measured as in Example 1. The calculated content of triolein was 98.1 mg/dl (based on theoretical value of 100 mg/dl).

The absorbance of the resulting aqueous solution was also measured at 340 nm on the basis of distilled water, to obtain 0.021.

The resulting aqueous solution was stored for 3 months at 4° C., 25° C. or 37° C. The triolein content measured 3 months later had not changed from said value for each solution. Further, each solution after 3 months was very stable without turbidity.

EXAMPLE 15

After 10 g of Emulgen 707 (polyoxyethylene higher alcohol; cloud point 33° C.; Kao Atlas K. K.) as the nonionic surfactant was dissolved in 90 ml of distilled water, 5 g of sodium chloride (builder) was added, and stirred at a room temperature (25° C.). The liquid became turbid, and into the turbid liquid, 2 g of triolein was added and vigorously stirred for about 2 hours. The resulting turbid liquid was diluted with 10 mM tris buffer (pH 7.9) to 10 times volume to obtain a transparent solution.

The absorbance of the resulting aqueous solution was measured at 340 nm on the basis of distilled water, to obtain 0.016.

For comparison, three formulations were prepared as in Examples 1–3, except that the builders were omitted. After stirring and supersonic treatment, the appearance of the formulations were observed, and the absorbances at 340 nm were measured. The results are shown in Table IV (listed in the column "conventional method") as well as those of the above Examples 1–3.

TABLE IV

| | Appearance | Absorbance |
|---|---|---|
| Example 1 | Transparent solution | 0.024 |
| Conventional method of Example 1 | Turbid liquid | 2.82 |
| Example 2 | Transparent solution | 0.021 |
| Conventional method of Example 1 | Turbid liquid | 2.12 |
| Example 3 | Transparent solution | 0.016 |
| Conventional method of Example 3 | Turbid liquid | 1.287 |

It is apparent from Table IV that the aqueous solution according to the present invention exhibits a higher transparency than the liquid prepared by the conventional method.

EXAMPLE 16

After 10 g of Emulgen 709 (polyoxyethylene higher alcohol; cloud point 56° C.; Kao Atlas K. K.) as the nonionic surfactant was dissolved in 90 ml of distilled water, 10 g of sodium chloride (builder) was added, and stirred at a room temperature (25° C.). The liquid became turbid, and into the turbid liquid, 1 g of lecithin was added and vigorously stirred for about 3 hours. The resulting turbid liquid was diluted with distilled water to 10 times volume to obtain a transparent solution.

The resulting aqueous solution was stored for 3 months at 4° C., 25° C. or 37° C. Each solution after 3 months was very stable without turbidity.

Although the present invention has been described with reference to specific embodiments, various changes and modifications obvious to those skilled in the art are deemed to be within the spirit, scope and concept of the invention.

We claim:

1. A method of determining human pancreatic lipase in a sample, comprising the steps of:
   (1) placing the sample in contact with a transparent aqueous solution containing a triglyceride as substrate in the presence of an agent for accelerating lipase activity to hydrolyze the triglyceride to liberate fatty acids; and
   (2) determining human pancreatic lipase by measuring an amount of the liberated fatty acids,
      wherein the transparent aqueous solution containing the triglyceride has been prepared by the steps of:
      (a) adding the triglyceride to an aqueous solution containing a nonionic surfactant to form a mixture;
      (b) adding a builder, selected from the group consisting of a salt of an inorganic acid and a salt of organic acid, to the mixture to lower the cloud point of the nonionic surfactant-containing aqueous solution to about room temperature; and
      (c) diluting the mixture with water or an aqueous buffer solution while stirring to form a transparent solution.

2. A method of determining human pancreatic lipase in a sample, comprising the steps of:
   (1) placing the sample in contact with a transparent aqueous solution containing a triglyceride as substrate in the presence of an agent for accelerating lipase activity and monoglyceride lipase to hydrolyze the triglyceride to liberate fatty acids and glycerol; and
   (2) determining human pancreatic lipase by measuring amount of the liberated fatty acids or glycerol,
      wherein the transparent aqueous solution containing the triglyceride has been prepared by the steps of:
      (a) adding the triglyceride to an aqueous solution containing a nonionic surfactant to form a mixture;
      (b) adding a builder, selected from the group consisting of a salt of an inorganic acid and a salt of an organic acid, to the mixture to lower the cloud point of the nonionic surfactant-containing aqueous solution to about room temperature; and
      (c) diluting the mixture with water or an aqueous buffer solution while stirring to form a transparent solution.

3. A process according to claim 1 wherein the transparent solution is lyophilized.

* * * * *